United States Patent [19]

Ridgway et al.

[11] Patent Number: 4,725,440

[45] Date of Patent: Feb. 16, 1988

[54] ANTIFUNGAL PASTILLE FORMULATION AND METHOD

[75] Inventors: Frank Ridgway; Michael D. Ward, both of Merseyside, England

[73] Assignee: E. R. Squibb & Sons, Inc., Princeton, N.J.

[21] Appl. No.: 613,556

[22] Filed: May 24, 1984

Related U.S. Application Data

[63] Continuation-in-part of Ser. No. 477,203, Mar. 21, 1983, abandoned.

[30] Foreign Application Priority Data

Jul. 2, 1982 [GB] United Kingdom ................. 8219265

[51] Int. Cl.$^4$ ...................... A61K 9/20; A61K 35/12; A61K 35/56; A61K 31/74
[52] U.S. Cl. ...................................... 424/465; 424/78; 424/95; 514/252; 514/398; 514/453; 514/460; 514/626
[58] Field of Search ................... 424/181, 465, 78, 95; 514/252, 398, 453, 460, 626

[56] References Cited

U.S. PATENT DOCUMENTS

| | | | |
|---|---|---|---|
| 2,797,183 | 1/1952 | Hazen et al. | 167/65 |
| 2,949,401 | 8/1960 | Wershaw | 424/362 |
| 3,312,594 | 4/1967 | Cyr et al. | 424/362 |
| 4,018,918 | 4/1977 | Ayer et al. | 424/240 |

OTHER PUBLICATIONS

Remington's Pharmaceutical Sciences, 15th Edition (1975), p. 1606.
Physician's Desk Reference, 26th Edition (1972), pp. 1338-1339.
Remington's Pharmaceutical Sciences, 16th Edition (1980), p. 1583.

*Primary Examiner*—Leonard Schenkman
*Assistant Examiner*—Joseph A. Lipovsky
*Attorney, Agent, or Firm*—Lawrence S. Levinson; Burton Rodney

[57] ABSTRACT

An antifungal pastille formulation, preferably containing nystatin as the antifungal agent, is provided which is soft and smooth in texture and when dissolved slowly in the mouth does not cause irritation of and will not adhere to oral mucosa and yet distributes nystatin in sufficiently high saliva concentrations, throughout the oral cavity, for long enough periods of time so as to be particularly effective in the treatment of candidiasis in the oral cavity and esophagus. A method for treating candidiasis in the oral cavity and esophagus employing the antifungal pastille and a method for preparing a nystatin pastille formulation are also provided.

14 Claims, No Drawings

ANTIFUNGAL PASTILLE FORMULATION AND METHOD

REFERENCE TO OTHER APPLICATIONS

This application is a continuation-in-part of U.S. application Ser. No. 477,203, filed Mar. 21, 1983 now abandoned.

FIELD OF THE INVENTION

The present invention relates to smooth velvety soft antifungal pastilles or troches which are free of rough edges so that they may even be tolerated by patients suffering from candidiasis in the oral cavity and esophagus and therefore are particularly effective in the treatment thereof.

BACKGROUND OF THE INVENTION

Oral candidiasis is an extremely virulent, painful, and life-threatening disease for the aged and debilitated and is especially prevalent in care centers for the aged with chronic debilitating ailments, cancer hospitals and transplantation centers. Most patients suffering from oral candidiasis find it practically impossible to tolerate solid foods and even solid medicines since the pain caused by contact of solids with infected areas is unbearable. Therefore, such patients can only ingest liquids. The medical problems of these patients are compounded by the fact that the patients are usually already in a debilitated state brought on by an underlying disease such as cancer, diabetes, emphesema or serious bacterial, viral or other fungal infections even before contracting oral candidiasis. The inability of the patient to ingest solids most often results in a further weakening and debilitation which, added to the effects of the underlying illness, usually results in the death of the patient.

The treatment generally indicated for combatting oral candidiasis is the use of antifungal agents such as nystatin in topical form, such as oral suspension or tablets. In order to be optimally effective, the nystatin must be supplied to the infected areas and maintained at a constant effective saliva level over a sustained period of time. Unfortunately, in the case of many patients, especially those with buccal ulcers, the nystatin suspension will not remain in contact with infected areas for sufficiently long periods to effectively combat the infection. The nystatin suspension is too easily washed away from infected areas. Thus, the effectiveness of such nystatin treatment is drastically curtailed since the suspension will not usually remain in contact with infected areas for sufficiently long periods to combat the infection.

Furthermore, as indicated, in most victims of this virulent disease, pain caused by any irritation in the oral cavity and esophagus becomes so unbearable that the slightest additional discomfort in the infected areas such as caused by the use of conventional nystatin tablets cannot be tolerated. Presently, nystatin tablets or lozenges which are normally used are hard and develop rough edges as they dissolve in the mouth and thereby further contribute to irritation. Suspensions may not cause irritation; however, they suffer from the dangerous disadvantage that they do not remain in contact with infected areas for sufficiently long periods to effectively combat the infection.

U.S. Pat. No. 3,312,594 to Cyr et al discloses long-lasting troches or pastilles which do not disintegrate or lose their integrity for 30 minutes or more, and contain a medicament used in treating the oral cavity for oral lesions, oral moniliasis, stomatitis and the like. The Cyr et al troches or pastilles include an anhydrous adhesive, which functions as carrier or vehicle as well, formed of 30 to 40% pectin, 30 to 40% gelatin and 30 to 40% carboxymethylcellulose (% being based on total weight of all three components). The anhydrous combination adhesive of large quantities of pectin, gelatin and carboxymethylcellulose, when wetted, causes the troche containing same to adhere to the oral mucous membranes and thus basically remain in a single localized infected area for prolonged periods while slowly and gradually releasing medication.

Unfortunately, although the Cyr et al formulation is excellent for treating certain types of oral conditions, it is not particularly well tolerated by the patient suffering from oral candidiasis. As indicated, the Cyr et al troche does not readily disintegrate or lose its integrity due to the presence of an anhydrous adhesive as discussed above. Thus, it will not have the smooth velvety comfortable muscilagenous mouth feel which is necessary if it is to be tolerated by the suffering patient, but instead will be rough, sticky and irritatingly adhesive-like. Furthermore, the Cyr et al troche remains localized and does not provide for maximum distribution of medicine throughout the oral mucosa and thus would not be particularly effective against widespread oral infection.

An ideal medicament for treating a patient suffering from oral candidiasis is one in the form of a pastille which is at all times free of rough edges and which contains an effective antifungal agent, is smooth, velvety, comfortable and sufficiently muscilageous so that it can be tolerated in the oral cavity and will slowly dissolve without adhering to the oral muscous membrane to distribute antifungal agent throughout the oral mucosa so that the antifungal agent will be retained at the sites of infection for a sufficiently long time to permit efficacy. The present invention provides such an ideal medicament.

DESCRIPTION OF THE INVENTION

In accordance with the present invention, a novel antifungal formulation, preferably a nystatin formulation, is provided which is especially adapted for treatment of oral candidiasis and is comprised of a soft antifungal (preferably nystatin) pastille or troche which is soft, smooth, velvety, free of rough edges, is free of adhesive, anhydrous or otherwise, and contains at least 10% by weight moisture so that it will not adhere to oral mucosa and will dissolve within a period of from about 15 to about 90 minutes while it provides a persistent level of medication. The pastille of the invention is thickened with a smooth gelatinous material to prevent the formation of rough portions around the edges as it dissolves in the oral cavity.

The soft non-adhering antifungal pastille of the invention, when used orally, thus provides an effective soothing non-irritating treatment for candidiasis of the oral cavity, including treatment of buccal ulcers, and of the esophagus, whereby organisms embedded and thriving in tissues and pseudomembranous exudate of mucosal lesions are contacted with and exposed to an antifungal agent, such as nystatin, in sufficiently high concentrations for sustained periods of time to effect such treatment.

The non-adhesive antifungal pastille formulation of the invention includes an antifungal agent, such as nystatin, in an amount of from about 0.1 to about 6% by weight depending upon the particular antifungal agent employed, and sufficiently smooth soft velvety pastille carrier, for masking the taste of an antifungal agent which contains from about 2 to about 10% by weight gelatinous material, and bulking agent and/or sweetener such as, for example, from about 75 to about 95% by weight of one or more sugars, at least one of which sugars is in the form of an aqueous syrup to provide from about 10 to about 20% by weight moisture in the final product, all of the above % being based on the total weight of the pastille.

In addition, in accordance with the present invention, a method is provided for treating candidiasis in the oral cavity or esophagus of patients who are not able to tolerate other solid forms of an antifungal agent, which method includes the steps of administering to the oral cavity of a mammalian species, such as humans, cats, dogs and the like, in need of such treatment, a therapeutically effective amount of the antifungal pastille formulation as described herein and allowing the formulation to slowly dissolve in the oral cavity without adhering to the oral mucosa.

Further, in accordance with the present invention, a method is provided for forming a soft smooth nystatin formulation, which includes the steps of forming a nystatin concentrate which includes from about 5 to about 20% by weight nystatin based on a potency of 5000 units per mg of nystatin and from about 80 to about 95% by weight bulking agent, such as sugar syrup or fructose syrup, sorbitol syrup, lycasin syrup and the like, based on the weight of the concentrate which contains from about 33 to about 50% by weight water based on the weight of the bulking agent forming a separate pastille base which includes from about 60 to about 85% by weight of one or more bulking agents, such as sugars, sorbitol, mannitol, xylitol, lycasin or fructose, from about 15 to about 25% by weight water and from about 5 to about 10% by weight gelatinous material, all of the above % being based on the weight of the pastille base, combining the nystatin concentrate and the pastille base, and forming pastilles from the resulting mixture which pastilles contain from about 10 to about 20% by weight moisture.

Nystatin has a particularly unpleasant taste which is effectively masked by the formulation of the invention. Thus, the patient given the formulation of the invention will allow the formulation to slowly dissolve in his mouth without experiencing the unpleasant nystatin taste, so that the nystatin remains in contact with the oral cavity and thereafter slowly drips down the esophagus to provide medication for sufficient periods in both the oral cavity and esophagus to effectively combat the infected areas. As discussed above, this was not possible with the prior art tablets and suspensions.

The pastille formulation of the invention will contain one or more antifungal agents, preferably nystatin, in sufficient quantities to maintain an effective saliva concentration for sufficient periods of time so as to produce adequate kill time of *C. albicans*. Thus, the pastille formulation will contain from about 0.1 to about 6% by weight antifungal agent, such as nystatin, and preferably from about 1 to about 4% by weight based on the total formulation. In preferred embodiments, the formulation will provide from about 25,000 to about 500,000 and preferably from about 75,000 to about 250,000 units nystatin or from about 5 mg to about 100 mg and preferably from about 15 mg to about 50 mg nystatin per pastille based on a potency of 5000 units/mg nystatin, which may be administered up to 16 times per day or any convenient regimen, such as 1 or 2 pastilles 4 times a day.

Other antifungal agents which may be incorporated in the pastilles of the invention include, but are not limited to amphotericin B, griseofulvin, miconazole, ketoconazole, and other conventional topically active imidazole antifungal agents which may be administered orally.

In addition, the pastilles of the invention may include, together with the antifungal agent, one or more antibacterial agents which may be used to treat bacterial infections in the oral cavity, such as, for example, neomycin, gentamycin, tyrothricin, gramicidin, and other conventional topically active antibacterial agents which may be administered orally. The antibacterial agent may be employed in amounts of from about 0.05 to about 5% by weight of the total pastille formulation.

The pastille formulation of the invention may also include from about 0.05 to about 2% by weight of a local anesthetic to further relieve pain in the oral cavity as a result of fungal and/or bacterial infections. The anesthetic employed may be lidocaine, benzocaine or other local anesthetic.

The pastille formulation of the invention will include a soft gelatinous sweetened base which may be a sugar candy, gelatin, glycerinated gelatin, agar, polyvinyl alcohol, preferably combinations of sugar candy and gelatin or glycerinated gelatin, together with sufficient mucilage to give it form, and sufficient moisture to ensure that the pastille will not adhere to the oral mucosa. A discussion of troches or pastilles which may be employed herein and methods for preparing same is set out in Remington's "*Pharmaceutical Sciences*", Fifteenth Edition (Mack Publishing Co., Pa.), p. 1606.

In preferred formulations, the antifungal agent, such as nystatin, with or without one or more antibacterial agents and/or local anesthetics, will be formulated with gelatin together with one or more sugars and/or artificial sweeteners, preferably at least two different sugars such as sucrose in syrup form and granular form, dextrose monohydrate and/or liquid glucose and/or fructose and/or one or more polyhydric sugar alcohols, such as sorbitol, mannitol and/or xylitol or lycasin, to prevent sugar crystallization. The sugars together with the gelatinous material forms a thick soft smooth sweet carrier for the antifungal agent which is soothing to inflamed tissues in the oral cavity and masks the unpleasant taste and odor of the antifungal agent. Preferred flavor oils which may also be added to mask the taste and odor of the antifungal agent, such as nystatin, include cinnamon oil, aniseed oil and mixtures thereof.

The pastille may also contain base and/or acid, as needed, to control pH of the formulation during manufacture.

In preparing the pastille of the invention, the antifungal agent together with or without antibacterial agent and other solids will be processed so that they will have an average particle size of within the range of from about 1 to about 50 microns and preferably from about 3 to about 20 microns to ensure formation of the smooth velvety soft pastilles of the invention.

The pastille formulation of the invention may also be formulated in a sugar-free pastille base which may include any of the sugarless bulking agents and sweeteners as set out herein.

Regardless of the specific formulation and how it is made, pastille formulations suitable for use herein will contain relatively small quantities of gelatinous material of from about 2 to about 15% and preferably from about 5 to about 10% by weight gelatinous material to provide the desired soft texture, from about 75 to about 95% and preferably from about 85 to about 90% by weight bulking agent, such as sugars, fructose, polyhydric sugar alcohols and other bulking agents for the gelatinous material and sweet taste to mask the taste of the antifungal agent and from about 10 to about 20% by weight water or moisture to ensure that the pastille does not adhere to the oral mucosa.

In addition to gelatin, glycerin and/or gelatinous materials which may be present, the pastille formulation of the invention may include gum acacia and/or alginates. A typical sugarless pastille formulation containing gum acacia may include from about 20 to about 40% by weight sorbitol, from about 50 to about 70% by weight gum acacia and from about 10 to about 20% by weight water.

Other examples of sugars which may be employed in the pastille formulation of the invention in addition to or in place of those mentioned above include, for example, monosaccharides of 5 or 6 carbon atoms, such as arabinose, xylose, ribose, mannose, galactose, fructose or sorbose, mixtures of two or more of the foregoing monosaccharides; disaccharides, for example, lactose, maltose or cellobiose; polysaccharides, such as partially hydrolyzed starch or dextrin.

Examples of artificial sweeteners which may be employed herein alone or preferably together with any one or more of the aforementioned sugars include sodium, calcium or ammonium saccharin salts, dihydrochalcones, glycyrrhizin, dipotassium glycyrrhizin, glycyrrhizic acid ammonium salt, L-aspartyl-L-phenylalanine methyl ester (aspartame), the sodium or potassium salt of 3,4-dihydro-6-methyl-1,2,3-oxathiazine-4-one2,2-dioxide (Ace-sulfame-K), as well as *Stevia rebaudiana* (Stevioside), *Richardella dulcifica* (Miracle Berry), *Dioscoreophyllum cumminsii* (Serendipity Berry), cyclamate salts, and the like, or mixtures of any two or more of the above.

The flavoring which may be present to further mask taste and odor of nystatin may comprise synthetic flavors and oils derived from plants, leaves, flowers, fruit, etc. Representaive flavor oils which may be employed include acids such as adipic, succinic and fumaric acid, citrus oils such as lemon oil, orange oil, lime oil, grapefruit oil, fruit essences such as apple essence, pear essence, peach essence, strawberry essence, apricot essence, raspberry essence, cherry essence, plum essence, pineapple essence, as well as the following essential oils: peppermint oil, spearmint oil, mixtures of peppermint oil and spearmint oil, clove oil, bay oil, anise oil, eucalyptus oil, thyme oil, cedar leaf oil, cinnamon oil, oil of nutmeg, oil of sage, oil of bitter almonds, cassia oil, and methylsalicylate (oil of wintergreen).

The antifungal pastille of the invention may contain other conventional ingredients employed in pastille or troche formulations as will be apparent to those skilled in the art such as antifoam agents such as silicone antifoam, colorants, preservatives and flavors.

Preferred soft nystatin pastille formulations are set out below:

| Ingredient | Mg/pastille |
| --- | --- |
| Nystatin (micropulverized) (*potency of 5000 units/mg) | 15 to 25 mg* |
| Sugar syrup (sucrose + water) (60 to 66% solids, 34 to 40% water) | 150 to 200 mg |
| Sucrose (granular) | 500 to 750 mg |
| Dextrose (monohydrate) | 100 to 200 mg |
| Liquid glucose (corn syrup, 40 to 60% solids, 60 to 40% water) | 750 to 1000 mg |
| Gelatin | 108 to 180 mg |
| Flavor oils | 5 to 40 mg |
| Total moisture present after processing | 200 to 400 mg |
| Optional Ingredient | |
| Antifoam or | 0.1 to 1 mg |
| Bases and acids to adjust pH in 6.0 to 7.5 range | |

As indicated, the pastille formulation of the invention may be prepared employing conventional pastille formulating an processing techniques.

In a preferred embodiment, the nystatin pastille formulation of the invention may be prepared as follows. The nystatin, with or without one or more antibacterial agents and anesthetics, is dispersed in sucrose syrup or other bulking agent as set out above to give a 5 to 15% concentrate. Thereafter, the granular sucrose (or other sweetener or bulking agent), liquid glucose and dextrose are dissolved in water, boiled at 105° to 110° C., and cooled to below about 60° C. under vacuum to form a syrup. The gelatinous material, preferably gelatin, previously dissolved in water, is added to the syrup. The flavors are added and the pH of the syrup is adjusted to 6.8 to 7.2 using for example, potassium hydroxide, sodium hydroxide or sodium citrate and concentrated hydrochloric acid, or citric acid, as needed. Thereafter, the nystatin concentrate is added to the syrup and thoroughly mixed therein.

The resulting mixture is poured into starch molds and dried at room temperature under controlled humidity (30 to 60% relative humidity). After 5 to 7 days, the pastilles are separated from the starch molds, sorted, oiled with light liquid paraffin (0.5 to 2.0%) and packed. The final weight of each of the pastilles is between 1.8 to 1.9 g. Alternatively, the above mixture may be cast into sheets and cut to desired size and shape.

The following Examples represent preferred embodiments of the invention.

EXAMPLE 1

A nystatin pastille formulation having a composition as set out below was prepared as follows.

| Formulation | |
| --- | --- |
| Ingredient | Mg/pastille |
| Nystatin (micropulverized) | 22 |
| Sucrose syrup (66% solids) | 180 |
| Sugar granular | 625 |
| Dextrose monohydrate | 150 |
| Liquid glucose | 825 |
| Gelatin | 150 |
| Silicone antifoam | 0.4 |
| Cinnamon oil | 5 |
| Aniseed oil | 15 |
| Potassium hydroxide solution 50% | q.s. |
| Hydrochloric acid | q.s. |

-continued

| Ingredient | Formulation Mg/pastille |
|---|---|
| Purified water | q.s. to 2000** |

*Based on a potency of 5000 units/mg Includes a 10% overage to give 110,000 units/pastille
**Removed by drying - but final pastille formulation contains about 14% by weight moisture The nystatin was dispersed in syrup to give approximately a 10% concentrate. The sugar, liquid glucose and dextrose monohydrate were dissolved in water, boiled at 107° C. and cooled to about 60° C. under vacuum. The gelatin, previously dissolved in hot water, was added to the syrup. The flavors and antifoam are added and the pH of the pastille base was adjusted to 6.8 to 7.2 using potassium hydroxide solution and concentrated hydrochloric acid. Finally, the nystatin/syrup concentrate was added to the bulk and thoroughly mixed.

The pastilles were poured into starch molds and dried at room temperature under controlled humidity (approx. 35% RH). After five days the pastilles were separated from the starch mold, sorted, oiled with light liquid paraffin (0.5 to 1%) and then packed. The final weight of the pastille was between 1.8 and 1.9 g.

The resulting nystatin pastille is a yellow to a light brown gelatin based pastille containing 100,000 units of nystatin activity. It is soft and smooth in texture and is designed to dissolve slowly in the mouth, without formation of rough edges and without adhering to the oral mucosa, for the treatment of oral candidiasis.

EXAMPLE 2

A nystatin pastille formulation having a composition as set out below was prepared as follows.

| Ingredient | Formulation Mg/pastille |
|---|---|
| Nystatin (micropulverized) | 22* |
| Sugar pulverized | 120 |
| Sugar granular | 625 |
| Dextrose monohydrate | 150 |
| Liquid glucose | 825 |
| Gelatin | 150 |
| Silicone antifoam | 0.4 |
| Cinnamon oil | 5 |
| Aniseed oil | 15 |
| Potassium hydroxide solution 50% | q.s. |
| Hydrochloric acid | q.s. |
| Purified water | q.s. to 2000** |

*Based on a potency of 5000 units/mg Includes a 10% overage to give 110,000 units/pastille
**Removed by drying - but final pastille formulation contains about 14% by weight moisture The nystatin was mixed with powdered sugar and the mixture was passed through a swing hammer mill to break down the aggregates of nystatin. The sugar, liquid glucose and dextrose monohydrate were dissolved in water, boiled at 107° C. and cooled to about 60° C. under vacuum. The gelatin, previously dissolved in hot water, was added to the syrup. The flavors and antifoam were added and the pH of the pastille base was adjusted to 6.8 to 7.2 using potassium hydroxide solution and concentrated hydrochloric acid. Finally, the nystatin/milled sugar concentrate was added to the bulk and thoroughly mixed.

The pastilles were poured into starch molds and dried at room temperature under controlled humidity (approx. 35% RH). After five days the pastilles were separated from the starch mold, sorted, oiled with light liquid paraffin (0.5 to 1%) and then packed. The final weight of the pastille was between 1.8 and 1.9 g.

The resulting nystatin pastille is a yellow to a light brown gelatin based pastille containing 100,000 units of nystatin activity. It is soft and smooth in texture and is designed to dissolve slowly in the mouth, without formation of rough edges and without adhering to the oral mucosa, for the treatment of oral candidiasis.

EXAMPLE 3

A nystatin pastille formulation having a composition as set out below was prepared as follows.

| Ingredient | Formulation Mg/pastille |
|---|---|
| Nystatin (micropulverized) | 22* |
| Sugar granular | 745 |
| Dextrose monohydrate | 150 |
| Liquid glucose | 825 |
| Gelatin | 150 |
| Silicone antifoam | 0.4 |
| Cinnamon oil | 5 |
| Aniseed oil | 15 |
| Potassium hydroxide solution 50% | q.s. |
| Hydrochloric acid | q.s. |
| Purified water | q.s. to 2000** |

*Based on a potency of 5000 units/mg Includes a 10% overage to give 110,000 units/pastille
**Removed by drying - but final pastille formulation contains about 14% by weight moisture The sugar, liquid glucose and dextrose monohydrate were dissolved in water, boiled at 107° C. and cooled to about 60° C. under vacuum. The gelatin, previously dissolved in hot water, was added to the syrup. The flavors and antifoam were added and the pH of the pastille base was adjusted to 6.8 to 7.2 using potassium hydroxide solution and concentrated hydrochloric acid. Finally, the nystatin was added to the bulk and thoroughly mixed.

The pastilles were poured into starch molds and dried at room temperature under controlled humidity (approx. 35% RH). After five days the pastilles were separated from the starch mold, sorted, oiled with light liquid paraffin (0.5 to 1%) and then packed. The final weight of the pastille was between 1.8 and 1.9 g.

The resulting nystatin pastille is a yellow to a light brown gelatin based pastille containing 100,000 units of nystatin activity. It is soft and smooth in texture and is designed to dissolve slowly in the mouth, without formation of rough edges and without adhering to the oral mucosa, for the treatment of oral candidiasis.

EXAMPLE 4

A sugarless nystatin pastille formulation having a composition as set out below is prepared as follows.

| Ingredient | Formulation Mg/pastille |
|---|---|
| Nystatin (micropulverized) | 22 |
| Sorbitol syrup (70% solids) | 180 |
| Sorbitol granular | 625 |
| Dextrose monohydrate | 150 |
| Liquid glucose | 825 |
| Gelatin | 150 |
| Silicone antifoam | 0.4 |
| Cinnamon oil | 5 |
| Aniseed oil | 15 |
| Potassium hydroxide solution 50% | q.s. |
| Hydrochloric acid | q.s. |

| Formulation | |
|---|---|
| Ingredient | Mg/pastille |
| Purified water | q.s. to 2000** |

*Based on a potency of 5000 units/mg Includes a 10% overage to give 110,000 units/pastille
**Removed by drying - but final pastille formulation contains about 14% by weight moisture The nystatin is dispersed in sorbitol syrup to give approximately a 10% concentrate. The sorbitol, liquid glucose and dextrose monohydrate are dissolved in water, boiled at 107° C. and cooled to about 60° C. under vacuum. The gelatin, previously dissolved in hot water, is added to the syrup. The flavors and antifoam are added and the pH of the pastille base was adjusted to 6.8 to 7.2 using potassium hydroxide solution and concentrated hydrochloric acid. Finally, the nystatin/syrup concentrate is added to the bulk and thoroughly mixed.

The pastilles are poured into starch molds and dried at room temperature under controlled humidity (approx. 35% RH). After five days the pastilles are separated from the starch mold, sorted, oiled with light liquid paraffin (0.5 to 1%) and then packed. The final weight of the pastille was between 1.8 and 1.9 g.

The resulting nystatin pastille is a yellow to a light brown gelatin based sugar-free pastille containing 100,000 units of nystatin activity. It is soft and smooth in texture and is designed to dissolve slowly in the mouth, without formation of rough edges and without adhering to the oral mucosa, for the treatment of oral candidiasis.

What is claimed is:

1. A method for treating candidiasis in the oral cavity and/or esophagus which comprises administering to the oral cavity of a mammalian species in need of treatment a therapeutically effective amount of a soft smooth non-adhesive antifungal pastille formulation which is free of rough edges and is especially adapted for treatment of candidiasis in the oral cavity and esophagus without causing irritation and allowing the formulation to slowly dissolve in the oral cavity for a period of from about 15 to about 90 minutes without adhering to the oral mucosa, said soft pastille formulation, consisting essentially of an antifungal agent in an amount of from about 0.1 to about 6% by weight of the total formulation, and a soft smooth pastille carrier therefor said pastille carrier being non-adhesive so that it will not adhere to the oral mucosa and consisting essentially of from about 2 to about 10% by weight gelatinous material, and one or more bulking agents and/or sweeteners for masking the taste of the antifungal agent, the total formulation containing from about 10 to about 20% by weight moisture so that it will not adhere to the oral mucosa and will dissolve in the oral cavity within a period of from about 15 to about 90 minutes.

2. The method as defined in claim 1 wherein the antifungal agent is nystatin, amphotericin B, miconazole, kietoconazole or griseofulvin.

3. The method as defined in claim 2 wherein the antifungal agent is nystatin.

4. The method as defined in claim 3 wherein the pastille contains from about 25,000 to about 500,000 units of nystatin.

5. The method as defined in claim 1 wherein said one or more gelatinous materials is comprised of gelatin, glycerin, agar, gum acacia, polyvinyl alcohol or mixtures thereof.

6. The method as defined in claim 1 wherein the gelatinous material is gelatin.

7. The method as defined in claim 1 wherein said one or more bulking agents are comprised of sucrose, dextrose and corn syrup.

8. The method as defined in claim 1 wherein said antifungal agent has an average particle size of within the range of from about 1 to about 50 microns.

9. The method as defined in claim 1 wherein said pastille formulation includes only sugarless bulking agents and/or sweeteners.

10. The method as defined claim 1 further including one or more antibacterial agents in an amount of from about 0.05 to about 5% by weight.

11. The method as defined in claim 10 wherein said antibacterial agent is neomycin, gentamycin, gramicidin or tyrothricin.

12. The method as defined in claim 1 further including a local anesthetic.

13. The method as defined in claim 12 wherein said anesthetic is lidocaine.

14. The method as defined in claim 1 wherein the pastille formulation contains nystatin in an amount of from about 15 to about 25 mg per pastille based on a potency of 5000 units per mg and is administered in a single dose up to 16 times per day.

* * * * *